United States Patent [19]

Ferres et al.

[11] Patent Number: 4,673,573
[45] Date of Patent: Jun. 16, 1987

[54] NOVEL FIBRINOLYTIC ENZYME COMPOUNDS

[75] Inventors: Harry Ferres, Epsom; Richard A. G. Smith, Reigate; Andrew J. Garman, Betchworth, all of England

[73] Assignee: Beecham Group p.l.c., England

[21] Appl. No.: 689,846

[22] Filed: Jan. 9, 1985

[30] Foreign Application Priority Data

Jan. 11, 1984 [GB] United Kingdom ............... 8400653

[51] Int. Cl.$^4$ .................... C12N 9/72; C12N 9/68; C12N 9/48; C12N 9/96

[52] U.S. Cl. ................... 424/94.63; 424/85; 424/88; 424/101; 435/177; 435/180; 435/181; 435/185; 435/188; 435/215; 435/217; 436/547; 530/812; 530/363

[58] Field of Search ............... 435/177, 188, 180, 181, 435/185, 215, 217; 436/547; 260/112 B, 112 R; 424/85, 88, 94, 101

[56] References Cited

U.S. PATENT DOCUMENTS

| | | | |
|---|---|---|---|
| 4,082,612 | 4/1978 | Robbins et al. | 424/94 X |
| 4,134,792 | 1/1979 | Boguslaski et al. | 435/188 X |
| 4,232,119 | 11/1980 | Carlsson et al. | 260/112 B X |
| 4,275,000 | 6/1981 | Ross | 260/112 R |
| 4,285,932 | 8/1981 | Smith | 424/94 |
| 4,305,926 | 12/1981 | Everse et al. | 424/94 X |
| 4,464,468 | 8/1984 | Avrameas et al. | 435/181 X |
| 4,507,283 | 3/1985 | Smith | 424/94 |
| 4,530,900 | 7/1985 | Marshall | 435/188 X |
| 4,536,391 | 8/1985 | Miyazaki et al. | 260/112 R X |
| 4,545,988 | 10/1985 | Nakayama et al. | 435/177 X |
| 4,564,596 | 1/1986 | Maximenko et al. | 435/177 |
| 4,600,580 | 7/1986 | Smith | 424/94 |

FOREIGN PATENT DOCUMENTS

| | | |
|---|---|---|
| 009879 | 8/1979 | European Pat. Off. |
| 0028489 | 10/1980 | European Pat. Off. |
| 0109653 | 11/1983 | European Pat. Off. |
| 0151308 | 12/1984 | European Pat. Off. |
| 8404536 | 10/1983 | U.S.S.R. |

OTHER PUBLICATIONS

J. of Immunol. Methods, 35: 267-275 (1980), Terouanne et al.
Jackson and Tang Biochem., 21, 6620.
King, Li and Kouchoumian, 1978, Biochem., 17, 1449.
Carlsson, Drevin and Axen, 1978, J. Biochem., 173, 723, European Search Report.
Japanese Abstract JP-A-5411219-Derwent Abstract, Chem. Absts. 136275e, 1979.

*Primary Examiner*—Howard E. Schain
*Attorney, Agent, or Firm*—Jacobs & Jacobs

[57] ABSTRACT

A fibrinolytically active protein conjugate comprising at least one optionally blocked fibrinolytic enzyme linked by way of a site other than the catalytic site responsible for fibrinolytic activity to at least one human protein.

Processes from making the conjugates and pharmaceutical compositions containing them are also described.

11 Claims, 8 Drawing Figures

NOVEL FIBRINOLYTIC ENZYME COMPOUNDS

This invention relates to protein conjugates for use in the treatment of thrombotic diseases. European Pat. No. 0,009,879 discloses derivatives of in vivo fibrinolytic enzymes which are useful therapeutic agents for treating thrombosis. The derivatives are characterised by the active catalytic site on the enzymes being blocked by a group which is removable by hydrolysis such that the pseudo-first order rate constant for hydrolysis is in the range $10^{-6} \text{sec}^{-1}$ to $10^{-3} \text{sec}^{-1}$.

It has now been found that fibrinolytic enzymes can be modified by linking to human proteins to give conjugates which retain fibrinolytic activity have slow physiological clearance rates, and/or improved in-vivo activity.

The term 'fibrinolytic enzyme' is used herein to mean any enzyme or proenzyme which demonstrates in vivo fibrinolytic activity as defined in published European Pat. No. 0,009,879 and includes enzymes which are obtainable from mammalian urine, blood or tissues or by recombinant DNA methods and which can activate plasminogen.

European Published Patent Application No. 0 109 653 (published 30.5.84) designating states Switzerland, Germany, France, Great Britain, Italy, Liechtenstein, Netherlands and Sweden discloses a process for producing a conjugate consisting of a protein adsorbable by fibrin (specifically plasmin heavy chain) with urokinase in the presence of a protein coupling reagent represented by the formula:

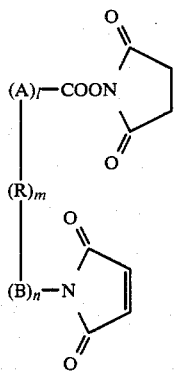

wherein R is phenylene or cycloalkylene, A is lower alkylene, B is lower alkylene which may optionally be substituted by lower alkylthio or phenyl-lower alkylthio, and l, m and n are each 0 or 1 provided that l, m and n are not 0 at the same time.

According to the present invention, there is provided a protein conjugate comprising at least one optionally reversibly blocked fibrinolytic enzyme linked by way of a site other than the catalytic site responsible for fibrinolytic activity to at least one human protein.

Conjugates of the invention may have the stoichiometry $$C_i D_j$$

where C is a fibrinolytic enzyme, D is a human protein and i or j can be an integer of 1–4. Preferably i and j are 1, 2 or 3. Most preferably i and j are 1.

Preferably the enzyme and the human protein are linked by means of a conventional-type bridging group such as a group of formula (I)

$$-A-R-B- \qquad (I)$$

in which each of A and B, which may be the same or different, represents $$-\overset{\overset{\displaystyle O}{\|}}{C}-, \quad -\overset{\overset{\displaystyle NH_2^+}{\|}}{C}-$$

or a bond, and R is a linking group containing one or more $-(CH_2)-$ units. Examples of R include $$-(CH_2)_n-, \quad -(CH_2)_p-S-S-(CH_2)_q-, \text{ and}$$

$$-(CH_2)_p-\underset{\underset{\displaystyle OH}{|}}{CH}-\underset{\underset{\displaystyle OH}{|}}{CH}-(CH_2)_q-$$

in which n is an integer suitably of at least 2 and preferably of at least four, and p and q are integers preferably of at least 2

R may include moieties which interact with water to maintain the water solubility of the linkage and suitable moieties include $$-\underset{\underset{\displaystyle O}{\|}}{C}-\underset{\underset{\displaystyle H}{|}}{N}-, \quad -\underset{\underset{\displaystyle O}{\|}}{C}-\underset{\underset{\displaystyle Me}{|}}{N}, \quad -S-S-, \quad -\underset{\underset{\displaystyle |}{|}}{CH}-OH, \quad -\underset{\underset{\displaystyle O}{\|}}{\overset{\overset{\displaystyle O}{\|}}{S}}-,$$

$$-\overset{\overset{\displaystyle O}{\|}}{C}-O, \quad -(CH_2CH_2-O)_m- \text{ and } -\underset{\underset{\displaystyle COOH}{|}}{CH}-$$

wherein m is an integer of 2 or greater.

Examples of suitable fibrinolytic enzymes are tissue-type plasminogen activators (t-PA), such as melanoma plasminogen activator, and urokinase (high or low molecular weight) and pro-urokinase.

Examples of suitable human proteins are plasma proteins which have long physiological clearance rates and the preferred minimum molecular weight of such proteins is about 30,000.

Specific examples of suitable human plasma proteins are plasminogen, serum albumin, fibrinogen, thyroglobulin, immunoglobulin.

Further examples of suitable human plasma proteins are fibrinolytic enzymes optionally irreversibly or reversibly blocked at the active centre thereof, provided that when the fibrinolytic enzyme is plasmin, the active centre thereof is reversibly blocked as described below or irreversibly inactivated by an inhibitor.

Suitable inhibitors are standard inhibitors such as diisopropylphosphofluoridate or N-α-tosyl-L-lysine chloromethylketone.

The fibrinolytic enzyme(s) in the conjugate of the invention may optionally be blocked by a removable group, as described in the above European Pat. No. 0,009,879. Preferred blocking groups are those which provide a pseudo-first order rate constant for hydrolysis of from $10^{-5}$ to $10^{-3} \text{ sec}^{-1}$, and particularly preferred blocking groups are 2- or 4-aminobenzoyl groups, such as those disclosed in published European Patent Application No. 0091240.

The fibrinolytic enzyme may be blocked according to the methods disclosed in the European Pat. No 0,009,879 or published European Patent Application No. 0091240.

Examples of conjugates of the invention include the following:

Reversibly blocked urokinase linked to human albumin;
Reversibly blocked urokinase linked to plasminogen;
Urokinase linked to human serum albumin;
Urokinase linked to reversibly blocked plasmin;
Reversibly blocked urokinase linked to reversibly blocked plasmin;
Tissue-type plasminogen activator linked to human serum albumin;
Tissue-type plasminogen activator linked to immunoglobulin G;
Tissue-type plasminogen activator linked to blocked plasmin; and
Tissue-type plasminogen activator linked to fibrinogen.

Further according to the present invention there is provided a process for preparing a fibrinolytically active protein conjugate as described above which process comprises reacting together an optionally blocked fibrinolytic enzyme and a human protein, one of which has been modified to include a linking group and the other of which has optionally been modified to include a protein attachment group; and thereafter if desired optionally blocking any fibrinolytic enzyme.

Suitable linking groups are derived from a linking agent of formula (II)

$$X-R_1-Y \qquad (II)$$

in which $R_1$ is a group as defined for R in formula (I), X and Y are functional groups reactable with surface amino acid groups, preferably a lysine (—NH₂) or cysteine (—SH) group or the N-terminal amino group, on a protein molecule.

When X is identical to Y, the linking agent is homobifunctional and can give rise to non-conjugative modifications due to the reaction of one end of the agent molecule with water and the other end with protein. Therefore, preferred agents are those wherein X is different from Y, and these are known as heterobifunctional agents. Each end of the agent molecule can be reacted in turn with each protein in separate reactions, and the production of non-conjugative modifications can thereby be limited.

Examples of heterobifunctional agents of formula (II) are

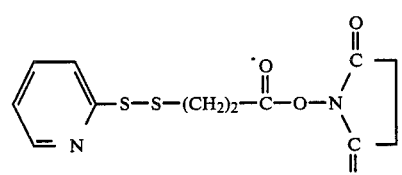

N—succinimidyl 3-(2-pyridyldithio)propionate (a)

-continued

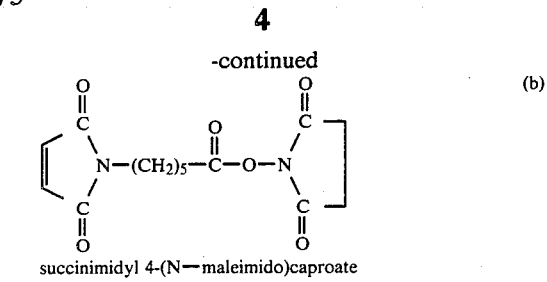

succinimidyl 4-(N—maleimido)caproate (b)

and

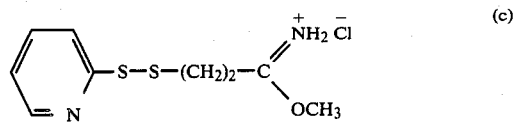

(c)

In formula (a), X is

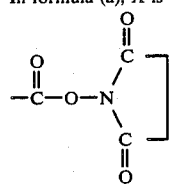

and Y is

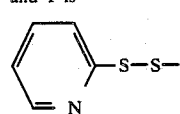

In formula (b) X is

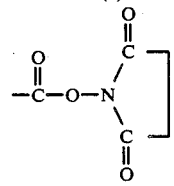

and Y is

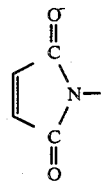

In formula (c) X is

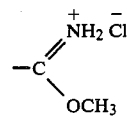

and Y is

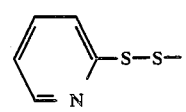

In each case Y is capable of reacting with a thiol group on the protein, which may be a native thiol or one introduced as a protein attachment group.

If either the human protein or the fibrinolytic enzyme to be conjugated does not contain a protein attachment group (e.g. a functionality capable of reacting with a heterobifunctional cross-linking group), then these may be introduced into the protein before conjugation is carried out. An example of a protein attachment group is a thiol group.

A particular process for making the protein conjugates of the invention comprises reacting a linking agent of formula (II) with an optionally reversibly blocked fibrinolytic enzyme and reacting the product with a human protein and which has been optionally modified by inclusion of a protein attachment group such as a thiol.

A further particular process for making the protein conjugates of the invention comprises reacting a linking agent of formula (II) with a human protein and reacting the product with an optionally reversibly blocked fibrinolytic enzyme which has been optionally modified to include a protein attachment group such as a thiol.

Suitably the human protein or enzyme is first modified by treatment with an amino acid side chain specific reagent to include a protein attachment group, in particular a thiol group.

The human protein or enzyme may be modified to introduce a protein attachment group in the form of a reactive thiol substituent by treating the protein with a thiolating agent, such as iminothiolane, homocysteine thiolactone or N-succinimidyl 3-(2-pyridyldithio)propionate, (with subsequent reduction) preferably in molar excess.

A linking group of formula (I) is suitably generated by a combination of group $R_1$ in formula II and protein attachment group(s).

For example human serum albumin can readily be linked to tissue plasminogen activator following modification with a thiolating agent. Reaction with 2-iminothiolane gives the albumin molecule modified by the inclusion of a protein attachment group, (a thiol group) as follows:

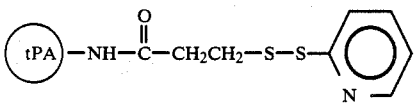

where the —NH— is derived from an albumin primary amine group. This molecule can now be coupled using a linking agent of formula (II). By way of illustration, agent structure (a) above will be used. This reagent is first coupled to the tissue plasminogen activator molecule to give the intermediate:

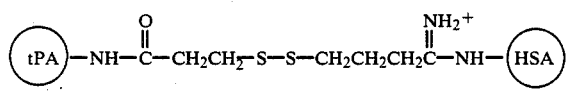

Reaction of these two derivatised proteins gives the conjugate:

tPA—NH—C(=O)—CH$_2$CH$_2$—S—S—CH$_2$CH$_2$CH$_2$C(=NH$_2^+$)—NH—HSA

In this conjugate, the group A comprises

and group B comprises

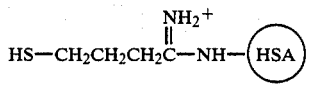

in structure I, whilst R is $(CH_2)_2$—S—S—$(CH_2)_3$.

The optional blocking of the active centre of the fibrinolytic enzyme(s) may be performed at any stage of the process except if the human protein to be conjugated is plasminogen. In this case the blocking needs to be performed before conjugation. If the blocking is performed early in the reaction sequence, a low concentration of blocking agent in the buffers may be required to maintain the blocking during subsequent stages.

The fibrinolytic enzymes and human protein are reacted with either the linking agent or the reagent for introducing protein attachment group by typically adding an excess of the reagent to the protein, usually in a neutral or moderately alkaline buffer, and after reaction removing low molecular weight materials by gel filtration or dialysis. The precise conditions of pH, temperature, buffer and reaction time will depend on the nature of the reagent used and the human protein or fibrinolytic enzyme employed, but should be chosen so that the degree of modification obtained is suitable for conjugation reactions. Preferably this should be in the range 0.5 to 4.0 moles/mole. The pH may also be controlled by use of a pH stat apparatus.

Suitable reagents for introducing thiols include iminothiolane, homocysteine thiolactone or N-succinimidyl 3-(2-pyridyldithio)propionate (with subsequent reduction).

The conjugation reaction is suitably performed by mixing the appropriately modified human protein and fibrinolytic enzyme in an approximately neutral buffer. The molar ratio is suitably approximately equimolar but may be varied in order to obtain the required degree of conjugation. Other reaction conditions e.g. time and temperature should be chosen to obtain the desired degree of conjugation. If thiol exchange reactions are involved, the reaction should preferably be carried out under an atmosphere of nitrogen.

After the conjugation reaction, the desired conjugate(s) can be isolated by a number of chromatographic procedures such as gel filtration, ion-exchange chromatography, affinity chromatography or hydrophobic interaction chromatography. These procedures may be either low pressure or high performance variants.

The conjugate may be characterised by a number of techniques including low pressure or high performance gel filtration, SDS polyacrylamide gel electrophoresis (optionally combined with fibrin overlaly zymography) or iso-electric focussing.

The methodology for reversible blocking of fibrinolytic enzyme active centres is described in European Pat. No. 0 009,879 and published European Patent Application No. 0091240 mentioned above.

The methodology employed to make these conjugates may give rise to a range of higher molecular weight species of general structure $C_iD_j$ wherein i and/or j are greater than 1. These high molecular weight species or mixtures thereof or mixtures of 1:1 conjugates with higher molecular weight species also constitute part of the invention.

The protein conjugate of this invention is preferably administered as a pharmaceutical composition.

Accordingly the present invention also provides a pharmaceutical composition comprising the conjugate of the invention in combination with a pharmaceutically acceptable carrier.

The compositions according to the invention may be formulated in accordance with routine procedures as pharmaceutical compositions adapted for intravenous administration to human beings.

Typically compositions for intravenous administration are solutions of the sterile derivative in sterile isotonic aqueous buffer. Where necessary the composition may also include a solubilising agent to keep the conjugate in solution and a local anaesthetic such as lignocaine to ease pain at the site of injection. Generally, the conjugate will be supplied in unit dosage form for example as a dry powder or water free concentrate in a hermetically sealed container such as an ampoule or sachette indicating the quantity of fibrinolytic enzyme in activity units. Where the conjugate is to be administered by infusion, it will be dispensed with an infusion bottle containing sterile pharmaceutical grade 'Water for Injection' or saline. Where the conjugate is to be administered by injection, it is dispensed with an ampoule of 'Water Injection' or saline for injection. The injectable or infusable composition will be made up by mixing the ingredients prior to administration.

The quantity of material administered will depend upon the amount of fibrinolysis required and the speed with which it is required, the seriousness of the thromboembolic condition and position and size of the clot. The precise dose to be employed and mode of administration must per force in view of the nature of the complaint be decided according to the circumstances by the physician supervising treatment. However, in general, a patient being treated for a mature thrombus will generally receive a daily dose of from 0.02 to 3.0 mg/kg of body weight either by injection in up to five doses or by infusion.

No toxic effects are indicated within the above mentioned dosage range with the conjugates of the invention.

Accordingly, in a further aspect of the invention there is provided a method of treating thrombotic diseases, which comprises administering to the sufferer an effective non-toxic amount of the protein conjugate of the invention.

The following Examples illustrate the invention.

EXAMPLE 1

Preparation of an HSA-t-PA conjugate (i) Preparation of thiolated human serum albumin (HSA-SH)

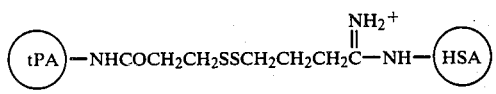

To a solution of HSA (Kabi, 200 mg/ml in saline) was added solid iminothiolane (10-fold molar excess) and the solution incubated at 37° C. for 1 hour. The product was removed from excess reagent by gel filtration through a column of Sephadex TM G25 M (PD-10) equilibrated with 50 mM $NH_4HCO_3$, 1 mM ε-aminocaproic acid and 1% D-mannitol. and lyophilised.

Titration with 5,5'-dithiobis-(2-nitrobenzoic acid) showed the presence of 2 moles thiol per mole HSA.

(ii) Preparation of 2-pyridyldithiopropionyl t-PA

Lyophilised t-PA was dissolved in 0.05M $NaH_2PO_4/Na_2HPO_4$ 0.1M NaCl 0.1M NaCl 0.01% Tween 80 buffer pH 7.4 at approximately 40,000 SU/ml and [$^{125}$I]t-PA (148 μCi/nmole) added to 7.5 μCi/ml. This solution was then gel filtered on Sephadex G25 M (PD-10) equilibrated with the same buffer. A 5 mM solution of N-succinimidyl 3-(2-pyridyldithio) propionate in dry ethanol was then added to a final concentration of 0.18 mM. The solution was incubated at ambient temperature for 30 minutes after which it was dialysed at 4° C. against the above buffer containing 10 mM ε-aminocaproic acid for 3 hours with one change of buffer.

(iii) Preparation of HSA-t-PA

To the solution of derivatised t-PA was added equimolar amounts of solid HSA-SH and the solution incubated at 4° C. for 16 hours under $N_2$. This was then applied to a LKB Ultropac TM TSK G-3000 SW h.p.l.c. gel filtration column equilibrated with 0.08M $NaH_2PO_4/Na_2HPO_4$ buffer pH 7.0 containing 0.32M NaCl and 20% (v/v) ethanol at 0.75 ml/min. Those fractions which previous column calibration had showed would contain the desired conjugate were pooled and desalted into 50 nM $NH_4HCO_3$, 0.2% D-mannitol by gel filtration on Sephadex G25 M and lyophilised.

The conjugate was characterised by 5% SDS polyacrylamide gel electrophoresis with Coomasie Blue staining, autoradiography and zymography (see Methods). These showed a predominantly single band of Mr 134,000 and a weaker band (ca. 10%) at Mr 203,000. The conjugate retained almost full (>74%) fibrinolytic activity on fibrin plates.

EXAMPLE 2

Preparation of 4 aminobenzoyl-urokinase plasminogen conjugate

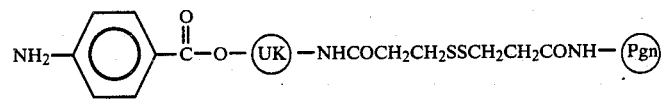

(i) Preparation of thiolated human lys-plasminogen

To a solution (45 μM) of human lys-plasminogen (Kabi) in 0.05M $NaH_2PO_4/Na_2HPO_4$ 0.1M NaCl pH 7.4 buffer was added N-succinimidyl 3-(2-pyridyldithio) propionate in dry ethanol (20 mM) to a final concentration of 144 μM and the reaction allowed to proceed for 30 minutes at ambient temperature. After dialysis (3 h, 4° C.) against the above buffer, 1M ε-aminocaproic acid was added to 10 mM and the pH adjusted to 4.5 with glacial acetic acid. Solid dithiothreitol was then added to a concentration of 50 mM and the solution stirred for 20 minutes at room temperature. Excess reagent was removed by passage through Sephadex G25 M equilibrated in the above phosphate buffer and 10 mM ε-aminocaproic acid. The resultant thiolated plasminogen solution (which was kept cold and under $N_2$) was analysed by titration with 5,5' dithiobis((2-nitrobenzoic acid) which showed 2.2 moles/mole thiol groups.

(ii) Preparation of 4-aminobenzoyl (2-pyridyldithiopropionyl) urokinase

To a solution of low MW urokinase (Abbokinase 165,000 I.U./ml in the phosphate saline buffer was added [125I]urokinase (7.5 μCi/nmole) to 4 μCi/ml. N-succinimidyl 3-(2-pyridyldithio) propionate (20 mM) in dry ethanol was then added to 0.66 mM and the solution incubated at room temperature for 30 minutes. The solution was diluted 1.9 times by addition of buffer and dialysed against the buffer for 3 h at 4° C. with one buffer change. The enzyme was then active-centre acylated by treatment with 1 mM 4-amidinophenyl-4'-aminobenzoate (APAB, added as a 50 mM solution in dimethylsulphoxide) for 1 h at 0° C., then at room temperature for 15 minutes. After passage through Sephadex G 25 M (PD-10) equilibrated with 0.05M NaH$_2$PO$_4$/Na$_2$HPO$_4$, 0.1M NaCl, 0.1 mM APAB, pH 7.4, the derivative was assayed for 2-pyridyldithio groups by adding excess dithiothreitol and measuring the absorbance at 343 nm ($\epsilon=8080$) due to the released 2-pyridylthione. 4.6 moles/mole were detected.

(iii) Preparation of the conjugate

The derivatised plasminogen and acylated urokinase solutions were mixed together in proportions so as to give equimolar amounts of the two functional groups and the solution incubated at 4° C. for 16 hours in the presence of 0.1 mM APAB. This solution was then applied to a column (115 ml) of Sephacryl ™ S-300 equilibrated with 0.1 mM APAB, 10 mM EACA in the phosphate saline buffer run at 4° C. Those fractions which previous calibration had shown would contain the desired conjugate were pooled. After desalting into 20 mM NH$_4$HCO$_3$, 1.0% D-mannitol, the conjugate was lyophilised. 5% SDS-polyacrylamide gel electrophoresis showed predominantly one major band at Mr 115,000 and one band corresponding to unreacted plasminogen. The conjugate retained full activity on fibrin plates through the concentration response curve was not parallel to native urokinase, the conjugate being more active at low concentrations and less active at high concentrations (see FIG. 1). A portion of the conjugate was deacylated at 37° C. in the pH 7.4 phosphate saline buffer containing 20% glycerol, 10 mM ε-aminocaproic acid and 0.17 TIU/ml aprotinin. Deacylation was monitored by assaying at intervals against S-2444. First-order kinetics were observed and the deacylation rate constant found to be $2.08\times10^{-4}$ sec$^{-1}$.

EXAMPLE 3

Preparation of 4-aminobenzoyl urokinase-human serum albumin conjugate

(i) Preparation of 2-pridyldithiopropionyl urokinase

To a solution of low M$_r$ urokinase (Abbokinase) in the phosphate saline buffer (165,000 IU/ml) was added [125I] urokinase to 5 μCi/ml. N-succinimidyl 3-(2-pyridyldithio) propionate (20 mM) in dry ethanol was then added to 0.57 mM and the solution incubated at room temperature for 30 minutes. After dialysis against phosphate saline buffer (3 hours, one change) the derivative was characterised as described above. 3.2 moles 2-pyridyldithio groups per mole were detected.

(ii) Preparation of thiolated human serum albumin (HSA-SH)

This was achieved as described in Example 1 except that a 6-fold excess of iminothiolane was used. The degree of substitution obtained was 0.6 moles/mole.

(iii) Preparation of the conjugate

The derivatised urokinase and HSA solutions were mixed in proportions to give equimolar amounts of the two functional groups and the solution incubated at 4° C. for 16 hours, then at room temperature for 1.5 hours. This was then applied to a LKB Ultropac TSK G-3000 SW h.p.l.c. gel filtration column equilibrated in 0.5M NH$_4$OOCCH$_3$, 0.2% mannitol, 20% ethanol at 0.75 ml/min. Those fractions which column calibration had shown would contain the conjugate were pooled and lyophilised.

(iv) Active centre acylation of the conjugate

The lyophilisate was reconstituted in 0.1M tris (hydroxymethyl) aminomethane, 0.9% NaCl, 20% glycerol pH 7.4 at ca. 50,000 to 100,000 IU/ml and the pH adjusted to 7.4 with 1M tris (hydroxyxethyl) aminomethane. After cooling on ice, 50 mM 4 amidinophenyl-4'-aminobenzoate in dimethylsulphoxide was added to final concentration of 1 mM. The solution was incubated for 1 h at 0° C., then for 10 minutes at 25° C. It was then gel filtered at 4° C. into 50 mM NH$_4$HCO$_3$, 1% mannitol, using a Sephadex G 25 M PD-10 column, and lyophilised.

SDS-polyacrylamide gel electrophoresis of the conjugate showed, by autoradiography, one band at Mr 100,000. Coomassie Blue staining also showed the presence of excess unconjugated albumin and albumin dimer. On fibrin plates the conjugate was 2-fold less active than native urokinase.

EXAMPLE 4

Preparation of high molecular weight urokinase-human serum albumin conjugate

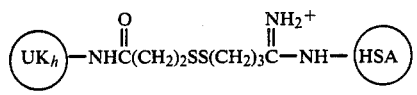

(i) Preparation of 2-pyridyldithiopropionyl urokinase 100,000 IU of urokinase (molecular weight 54,000, Serono) was dissolved in 2 ml of 0.05M NaH$_2$PO$_4$/Na$_2$HPO$_4$, 0.1M NaCl, 0.01% Tween 80 buffer, pH 7.4. A solution of 60 mM N-succinimidyl 3-(2-pyridyldithio)propionate in dry dimethylsulphoxide was added to a final concentration of 0.75 mM and the mixture incubated at 25° C. for 30 minutes. The solution was then passed down two PD-10 columns (Pharmacia) of Sephadex G-25 M equilibrated in the buffer as above and the protein fraction collected (volume 4 ml). The resultant 2-pyridyldithiopropionyl urokinase was assayed for 2-pyridyldithio groups by adding excess dithiothreitol and measuring the absorbance at 343 nm ($\epsilon = 8080$) due to the released 2-pyridylthione. 0.96 moles/mole were detected.

(ii) Preparation of thiolated human serum albumin

The procedure for preparing thiolated human serum albumin was as outlined in Example 1, except that the degree of modification was 1.3 moles of SH/mole of albumin.

(iii) Preparation of the conjugate

To a solution of 2-pyridyldithiopropionyl urokinase was added 8.5 mg of thiolated albumin and the solution was incubated under $N_2$ at ambient temperature for ca. 2 hours. This was then applied to a Sephacryl S-300 (Pharmacia) gel filtration column equilibrated in 100 mM $NH_4HCO_3$, 0.2%. D-mannitol. Fractions were assayed for protein concentration ($OD_{280}$) and amidolytic activity against the chromogenic substrate S-2444 (Kabi). Using these data a pool was made of the appropriate fractions containing the conjugate. Analysis of the pool by high performance liquid chromatography using a G-3000 SW gel filtration column (L.K.B.) indicated one major protein band accounting for 90% of the S-2444 activity with the remaining 10% associated with unreacted urokinase. The molecular weight of the main activity peak was found to be ca. 125,000 by comparison with Biorad molecular weight calibration proteins. Sodium dodecyl sulphate polyacrylamide electrophoresis with fibrin zymography indicated fibrinolytic activity at MW 100,000 and 54,000. The relative fibrinolytic activity of the conjugate was determined on human fibrin plates (0.4% w/v) against urokinase standards and found to possess ca. 50% of native urokinase activity.

EXAMPLE 5

Preparation of 4-aminobenzoyl high molecular weight urokinase human serum albumin conjugate 7.4 to determine its deacylation kinetics. The dilute solution was incubated at 37° C. and timed aliquots assayed for amidolytic activity against S-2444 (Kabi). The first order deacylation rate constant was found to be $2.1 \times 10^{-4}$ sec$^{-1}$. The fibrin plate activity of this conjugate was studied as described in Example 4, (iii) and found to be active.

EXAMPLE 6

Preparation of high molecular weight urokinase 4-aminobenzoyl plasmin conjugate

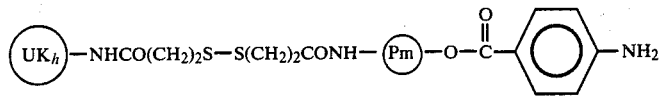

(i) Preparation of 2-pyridyldithiopropionyl urokinase

Urokinase (Serono, 500,000 IU) was dissolved in 1 ml of 0.05M $NaH_2PO_4/Na_2HPO_4$, 0.1M NaCl, 0.01% Tween 80 and N-succinimidyl 3-(2-pyridyldithio)propionate in dry dimethylsulphoxide (60 mM) was added to 0.75 mM and the reaction incubated at 25° C. for 30 minutes. Subsequent methodology was as described in Example 4 and in two batches prepared the degree of substitution was 1.66 and 1.34 moles/mole.

(ii) Preparation of thiolated 4-aminobenzoyl plasmin

A solution of human lys-plasminogen (Immuno) at 158 $\mu$M was dialysed against 200 volumes of 0.05M $NaH_2PO_4/Na_2HPO_4$, 0.1M NaCl at 4° C. for 24 hours and then centrifuged at 4000 rpm for 10 minutes. The supernatant was diluted to 42 $\mu$M in the above buffer with the addition of 4guanidinobutyric acid to 5 mM. N-succinimidyl 3-(2pyridyldithio)propionate (10 mM in dry dimethylsulphoxide) was added to 0.08 mM and the solution incubated at 25° C. for 15 minutes. This was passed down a Sephadex G-25 M gel filtration column (volume 77 ml) equilibrated in 0.1M tris (hydroxymethyl)aminomethane, 0.9% w/v NaCl, 20% v/v glycerol pH 7.4. The resultant 2-pyridyldithiopropionyl plasminogen was analysed as outlined in Example 4, typically the degree of substitution was 1.2 to 1.4 moles/mole. Activation of the plasminogen was at either ambient temperature with 20,000 IU of urokinase or 4° C. for ca. 20 hours with 10,000 IU. Following the confirmation of complete activation using the chromogenic substrate, S-2251, the plasmin active centre was acylated with 1

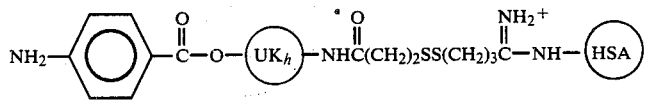

A portion of the lyophilised conjugate described in Example 4 was re-dissolved in 0.05M $NaH_2PO_4/Na_2HPO_4$, 0.1M NaCl, 0.01% Tween 80 pH 7.4 to a concentration of 26,750 SU/ml. The enzyme was then active centre acylated with 1 mM 4-amidinophenyl 4'-aminobenzoate (added as a 50 mM solution in dry dimethylsulphoxide) for 2 hours on ice. The acylated conjugate was then applied to a PD-10 G-25 M column (Pharmacia) equilibrated with 0.05M $NaH_2PO_4/Na_2HPO_4$, 0.1M NaCl, 0.01% Tween 80, 10 mg/ml bovine serum albumin. The protein peak was collected and a portion diluted 1:10 into 0.1M Tris (hydroxymethyl)aminomethane, 0.9% w/v NaCl, 20% v/v glycerol pH mM 4-amidinophenyl 4'-aminobenzoate added as a 50 mM solution in dry dimethylsulphoxide. Residual plasmin activity after 100 minutes on ice was typically 0.2%. The solution was brought to 1 mM $\epsilon$-aminocaproic acid equilibrated to ambient temperature under $N_2$, and the pH lowered to 4.5 by the dropwise addition of 50% acetic acid. Solid dithiothreitol was added to 50 mM and the solution incubated at ambient temperature for 15 minutes under $N_2$. The solution was then applied to a Sephadex G-25 M column (249 ml) equilibrated in 0.2% mannitol, 2 mM $\epsilon$-aminocaproic acid, 100 mM NH₄HCO₃, the protein peak was collected and freeze-dried. Titration with 5,5'-dithiobis-(2-nitrobenzoic acid) showed the presence of 0.37 moles thiol per mole 4-aminobenzoyl plasmin.

(iii) Preparation of the conjugate

The two batches of this conjugate were prepared using a molar ratio of pyridyldithiopropionyl to free SH groups of 2.7:1 and 1:1. After conjugation under N₂ at 4° C. for ca. 20 hours the solution was applied to a Sephacryl S-300 column (Pharmacia) primed with 5 ml 10 mg/ml bovine serum albumin and equilibrated in 0.2% mannitol, 100 mM NH₄HCO₃, 1 mM ε-aminocaproic acid, 2.55 TIU/1 aprotinin (Sigma). Fractions were assayed for protein (OD$_{280}$) and amidolytic activity against S-2444 (Kabi). Using these data a pool was made of the appropriate fractions containing the conjugate, and freeze-dried. A further passage down a Sephacryl S-300 column was performed on the reconstituted conjugate. A pool of the appropriate fractions was made as described previously and this was then lyophilised.

The deacylation rate constant for the hydrolysis of the 4-aminobenzoyl plasmin conjugate was not determined directly. However, a previous study (using methodology described in Example 5) of the deacylation kinetics of unconjugated 4-aminobenzoyl plasmin showed a first order rate constant of $1.1 \times 10^{-5}$ sec$^{-1}$ i.e. $t_{\frac{1}{2}} = 17$ hours.

EXAMPLE 7

Preparation of 4-aminobenzoyl urokinase-4-aminobenzoyl plasmin conjugate in Example 5 and found to be $1.3 \times 10^{-3}$ sec$^{-1}$. The conjugate was found to be active on fibrin plates.

EXAMPLE 9

Preparation of a tissue plasminogen activator human serum albumin conjugate

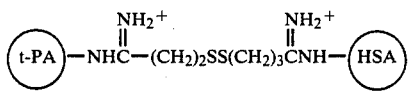

(i) Synthesis of 3-Mercaptopropionitrile

The material was produced in two steps from thiourea and 3-chloropropionitrile via 3-isothioureidopropionitrile by the method described by Traut et al (Biochem., 1973, 12, 3266).

(ii) Preparation of 3-(2'-Dithiopyridyl)propionitrile

3-Mercaptopropionitrile (500 mg, 5.75 mmole) in methanol (10 ml) was added to a solution of 2,2'-dipyridyl disulphide (1.26 g, 5.75 mmole) in methanol (10 ml), over a period of about fifteen minutes under an atmosphere of nitrogen. The solution, which turned pale green during the addition, was stirred for a further hour at room temperature. The solvent was removed by evaporation, and the residual oil was triturated with diethyl ether (25 ml). The yellow solid formed was removed by filtration and the ether solution was evaporated. The oil was chromatographed (10 g silica, dichloromethane eluant), and the least polar material was collected as a colourless oil (695 mg), the the title compound.

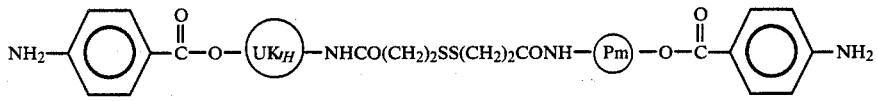

A portion of the lyophilised conjugate described in Example 6 was reconstituted in 0.05 M NaH₂PO₄/Na₂HPO₄, 0.1M NaCl, 0.01% Tween 80 to 5,600 SU/ml. Active centre acylation of the enzyme was achieved by addition of a 460 μM solution of 4-amidinophenyl-4-aminobenzoate in dry dimethylsulphoxide to a final concentration of 13.8 μM. After incubation at 4° C. for 7 hours, the solution was then passed down a PD-10 column of Sephadex G-25 M (Pharmacia) equilibrated in the above buffer and the protein peak collected in a total volume 2 ml. The deacylation rate constant of this material was determined as in Example 5 and found to be $2.5 \times 10^{-4}$ sec$^{-1}$. The material was active on fibrin plates.

EXAMPLE 8

Preparation of 4-N,N-dimethylaminobenzoyl urokinase-4-aminobenzoyl plasmin conjugate $^1$H nmr (CDCl₃)δ: 8.5 (1H, m, N—C<u>H</u>), 7.6 (2H, m, aryl-<u>H</u>), 7.20 (1H, m, aryl-<u>H</u>), 2.9 (4H, m, CH₂).

Infra red (thin film) 3040, 2920, 2240, 1585, 1560, 1450, 1420, 1280, 1120, 990, 760, 720 and 620 cm$^{-1}$.

(iii) Preparation of Methyl 3-(2'-dithiopyridyl)propionimidate ester hydrochloride A solution of hydrogen chloride gas (15.2 g) in methanol (20 ml) was prepared. This solution (1.5 ml) was added to the nitrile (500 mg) prepared above, and allowed to stand at 4° C. for ca. 18h. Diethyl ether (3 ml) was added and an oil was formed which solidified on standing. This was filtered and washed with a mixture of methanol and diethyl ether (1:3, 30 ml), an inert atmosphere being maintained throughout the procedure. The material was dried over phosphorus pentoxide in vacuo for 3h and the pale green crystalline compound

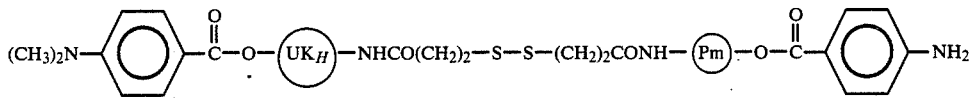

This conjugate was prepared as described in Example 7 except that a 460 μM solution of 4-amidinophenyl 4'-N N-dimethylaminobenzoate in dry dimethylsulphoxide was used for active centre acylation. The first order deacylation rate constant was determined as described (360 mg) stored at −18° C. over desiccant, m.p. 93°-5°. $^1$H nmr (d$^6$ DMSO): 7.2–8.7 (4H, m, aryl-<u>H</u>), 4.1 (3H, s, OC<u>H</u>₃) and 3.1 (4H, t, J=3H3, CH₂). Infra red (Nujol): 2500–3500 br, 1650, 1410, 1280, 1200, 1100, 990, 810, and 620 cm$^{-1}$.

(iv) Preparation of 2-pyridyldithiopropionimidyl-t-PA

To a solution of t-PA (70% 1-chain form, 270,000 SU/ml, 1 ml) in 20 mM NaH$_2$PO$_4$/Na$_2$HPO$_4$, 0.3 M NaCl, 0.1 M 4-guanidinobutyric acid 0.01% Tween 80, pH 7.4, was added 1 ml of 0.1 M sodium pyrophosphate/HCl buffer, pH 8.0 containing 0.1 M 4-guanidinobutyric acid and 0.01% Tween 80. The solution was stirred at room temperature and methyl 3-(2'-dithiopyridyl)propionimidate hydrochloride (3 mg) was added, maintaining the pH at 8.0 by addition of 0.5 M NaOH from an autoburette. After 5 minutes the solution was removed from the autoburette and allowed to stand at room temperature (ca. 22° C.) for 90 minutes. It was then de-salted at room temperature by passage down 2 Sephadex G-25 M PD-10 columns equilibrated with 0.05 M NaH$_2$PO$_4$/Na$_2$HPO$_4$, 0.1 M NaCl, 0.1 M 4-guanidinobutyric acid, 0.01% Tween 80.

(v) Preparation of the conjuqate

Thiolated HSA was prepared as described in Example 1 but using a 1.8 fold excess of iminothiolane. This gave a derivative with 0.77 moles SH per mole protein. 6.5 mg of this material was added to the above solution, which was allowed to react for 16 hours at 4° C. The conjugate was then isolated by chromatography at 4° C. on Sephacryl G-300 (130 ml column) equilibrated with 100 mM NH$_4$HCO$_3$, 0.2% D-mannitol (the column was primed with IgG (Sigma, 4 ml, 10 mg/ml) before use). Fractions which column calibration showed would contain the conjugate were pooled and lyophilised. On analytical hplc (system described in Example 1, iii) the conjugate was shown to have a molecular weight of 140,000 compared to Biorad MW calibration standards. The material possessed a high degree of activity on fibrin plates, ca. 60% of native t-PA.

Example 10

Preparation of a tissue plasminogen activator-human serum albumin conjugate

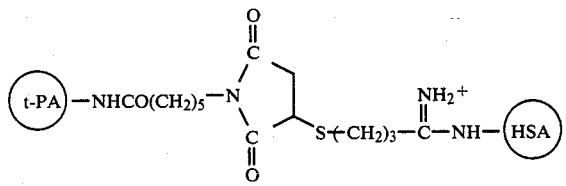

(i) Preparation of 2-maleimidocaproyl-t-PA

To a solution of 2-chain t-PA (130,000 SU/ml) in 20 mM NaH$_2$PO$_4$/Na$_2$HPO$_4$, 0.3 M NaCl, 0.1 M 4-guanidinobutyric acid, 0.01% Tween 80 pH 7.4 at ambient temperature was added 4.9 µl of a solution of N-(ε-maleimidocaproyloxy)succinimide (Sigma, 10 mM) in dry dimethylsulphoxide. After reaction at ambient temperature for 15 minutes, the solution was desalted into 0.05 M NaH$_2$PO$_4$/Na$_2$HPO$_4$, 0.1 M NaCl, 0.1 M 4-guanidinobutyric acid, 0.01% Tween 80, pH 7.4 using a PD-10 column of Sephadex G-25 M. The degree of substitution was assessed by back titration with 2-mercaptoethanol: to 250 µl of solution was added 250 µl of the above buffer and 20 µl of 200 µM 2-mercaptoethanol. After 20 minutes at 37° C. the thiol content was determined using 5,5'-dithiobis-(2-nitrobenzoic acid) and compared to a mercaptoethanol only control. The degree of substitution was found to be 1.05 moles maleimido groups per mole protein.

(ii) Preparation of the conjugate

To the above solution (1.75 ml) was added 2 mg thiolated HSA (according to Example 9). After incubation under N$_2$ at 4° C. for 16 hours the solution was applied to a Sephacryl S-300 column (100 ml) primed with HSA (Sigma, 5 ml, 10 mg/ml) equilibrated with 100 mM NH$_4$HCO$_3$, 0.2% D-mannitol. Relevant fractions were pooled and lyophilised. Analytical hplc according to Example 9 showed the molecular weight to be ca. 130,000. On fibrin plates the conjugate was fibrinolytically active (ca. 40% of native t-PA).

EXAMPLE 11

Preparation of a tissue plasminogen activator - fibrinogen conjugate

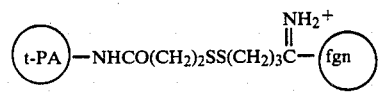

(i) Preparatin of thiolated fibrinogen

To a solution of human fibrinogen (Kabi, 10 mg protein/ml, 1.0 ml) in 0.05 M NaH$_2$PO$_4$/Na$_2$HPO$_4$, 0.1 M NaCl, 0.01% Tween 80 was added 20 µl of a freshly prepared (less than 0.5 minute) solution of 2-iminothiolane (Sigma, 2.02 mg/ml). After incubation at ambient temperature (ca. 22° C.) for 30 minutes, the solution was de-salted on a PD-10 Sephadex G-25 M column (Pharmacia) equilibrated in the above buffer to give a 2.0 ml protein fraction. A portion was assayed for thiol groups using 5,5'-dithiobis-(2-nitrobenzoic acid): 2.0 moles per mole protein were detected.

(ii) Preparation of 2-pyridyldithiopropionyl t-PA

To a solution of t-PA (70% 1-chain form, 130,000 SU/ml, 1.52 ml) in 20 mM Na$_2$HPO$_4$/NaH$_2$PO$_4$, buffer, 0.3 M NaCl, 0.1 M 4-guanidinobutyric acid, 0.01% Tween 80, pH 7.4 was added 6.8 µl of a solution of N-succinimidyl 3-(2-pyridyldithio)propionate (Pharmacia) in dry ethanol (30 mM) and the solution incubated at ambient temperature for 15 minutes. It was then desalted into 0.05 M NaH$_2$PO$_4$/Na$_2$HPO$_4$, 0.1 M NaCl, 0.1 M 4-guanidinobutyric acid, 0.01% Tween 80, pH 7.4 (4 ml) using 2 PD-10 Sephadex G-25 M columns (Pharmacia).

(iii) Preparation of the conjugate

The solutions obtained in (i) and (ii) above were mixed and 0.34 TIU aprotinin added. This was then incubated under N$_2$ for 16 hours at 4° C. during which time a precipitate formed. After centrifugation at 3,000 rpm for 10 minutes (MSE Chilspin) the supernatant was applied to a column of Sephacryl S-300 (40 ml) equilibrated with 100 mM NH$_4$HCO$_3$, 0.2% D-mannitol. The conjugate eluted as a broad peak at the excluded volume. On analytical hplc (according to Example 9) this peak had an apparent molecular weight of ca. 800,000. Since the gel filtration molecular weight of fibrinogen is 737,000 (Andrews, P., Biochem. J., 1965, 96, 595), this peak probably corresponds to a 1:1 conjugate. The material was active on fibrin plates.

EXAMPLE 12

Preparation of tissue-plasminogen activator IgG conjugate

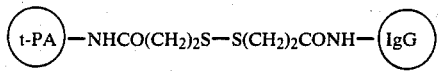

(i) Preparation of 2-pyridyldithiopropionyl IgG 100 mg of human IgG (Sigma) was dissolved in 1 ml of 0.05 M NaH$_2$PO$_4$/Na$_2$HPO$_4$, 0.1 M NaCl, 0.01% Tween 80. A solution of 60 mM N-succinimidyl 3-(2-pyridyldithio) propionate in dry dimethylsulphoxide was added to 1.2 mM and the reaction incubated at 25° C. for 30 minutes. It was then passed down a PD-10 column (Pharmacia) of Sephadex G-2 M equilibrated in the buffer as above. The resultant 2-pyridyldithiopropionyl IgG was assayed as described in Example 4 and 1.2 moles of pyridyldithio groups/mole of IgG were detected.

(ii) Preparation of thiolated tissue-plasminogen activator

A solution of 2-chain t-PA (130,000 SU/ml) in 20 mM NaH$_2$PO$_4$/Na$_2$HPO$_4$, 0.3 M NaCl, 0.1 M 4-guanidinobutyric acid, 0.01% Tween 80, pH 7.4 (2 ml) was treated with 10 λ of a 30 mM solution of N-succinimidyl 3-(2-pyridyldithio) propionate in dry ethanol. After a 15 minute incubation at ambient temperature the material was desalted as described above to give a 4 ml protein pool. This solution was reduced and analysed using the procedure outlined in Example 6 except that the incubation period was for forty minutes at ambient temperature. Analysis indicated 1.6 moles of sulphydryl groups/mole of activator.

(iii) Preparation of the conjugate

The 2-pyridyldithiopropionyl IgG and 2-thiolated activator were reacted under N$_2$ in a molar ratio of 2.8:1 at 4° C. for 20 hours then ambient temperature for 3 hours. This solution was applied to a Sephacryl S-300 gel filtration column equilibrated in 0.2% mannitol, 100 mM NH$_4$HCO$_3$ and primed with 2 ml of 20 mg/ml human IgG. Fractions were assayed for protein (OD$_{280}$) and amidolytic activity against S-2288 (Kabi). Appropriate fractions were pooled and lyophilised. Analysis of the conjugate by high performance liquid chromatography using a G-3000 SW gel filtration column (LKB) indicated one major high molecular peak accounting for 92% of the amidolytic activity. Sodium dodecyl sulphate polyacrylamide electrophoresis with fibrin zymography indicated fibrinolytic activity at positions corresponding to molecular weights of ca. 200,000 and 64,000. The conjugate was active on human fibrin plates.

EXAMPLE 13

Preparation of tissue plasminogen activator (4-aminobenzoyl) plasmin conjugate

Preparation of thiolated 4-aminobenzoyl plasmin

The procedure was that outlined in Example 6. Analysis indicated 0.36 moles of thio groups/mole of plasmin.

Preparation of 2-pyridyldithiopropionyl tissue activator

A solution of activator at 112,000 SU/ml was treated with a solution of 30 mM N-succinimidyl 3-(-2 pyridyldithio) propionate in dry dimethylsulphoxide to a concentration of 0.16 mM. The solution was incubated at 25° C. for 15 minutes and was then passed down 2 PD-10 columns of Sephadex G-25 M (Pharmacia) equilibrated in 0.05 M NaH$_2$PO$_4$/Na$_2$HPO$_4$, 0.1 M NaCl, 0.01% Tween 80, 0.1 M 4-guanidinobutyric acid to give a final pool of 5 ml.

Preparation of the conjugate

To 4 ml of 2-pyridyldithiopropionyl activator at 6.7 μM was added 9 mg of thiolated 4-aminobenzoyl plasmin. One trypsin inhibitor unit of aprotinin (Sigma) was added and the solution incubated at 4° C. for 22 hours under N$_2$. The solution was then applied to a Sephacryl S-300 (Pharmacia) gel filtration column equilibrated in 0.2% D-mannitol, 100 mM NH$_4$HCO$_3$, 1 mM ε-aminocaproic acid, 2.55 trypsin inhibitor units/litre aprotinin (Sigma) after priming with 20 mg/ml human IgG (4 ml). Fractions were assayed for protein (OD$_{280}$) and amidolytic activity against 1 mM S-2288 (Kabi). Using these data, the appropriate fraction was applied to a high performance liquid chromatography G-3000 SW gel filtration column (LKB). Fractions from this column were assayed as above and the appropriate fraction containing conjugate was found to be active on fibrin plates.

Methods (a) Chromogenic substrate assay

Urokinase and t-PA were assayed against the chromogenic substrates (KabiVitrum, Sweden) S-2444 and S-2288, respectively at a substrate concentration of 1 mM in 0.1 M triethanolamine.HCl pH 8.0 at 25° C. An SU is defined as the amount of activity that gives an O.D. increase of 0.001/min in 1 ml substrate in a 1 cm pathlength cell.

(b) Assay of fibrinolytic activity in the bloodstream of rats

Male Sprague-Dawley rats (300–400 g) were anaesthetized with pentobarbitone sodium (60 mg/kp i.p.). One carotid artery was cannulated for collection of blood samples. One femoral vein was cannulated for injection of heparin (50 U/kg) and compound under test. Approximately 5 min after heparinization, a pre-dose blood sample (0.8 ml) was taken and mixed with 0.1 volumes 129 mM trisodium citrate. The compound under test was then injected (1 ml/kg) over 10s. Further blood samples were taken exactly 1, 2, 4, 8, 16, 30 and 60 min later. Heparin treatment (50 U/kg) was repeated after the 30 min sample to maintain cannula patency. All citrated blood samples were kept on ice until the end of

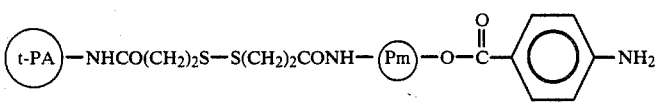

each experiment, then centrifuged at 1700 g for 15 min at 4° to obtain plasma. The euglobulin fraction was precipitated by adding 0.1 ml each plasma to 1.82 ml ice-cold 0.011% (v/v) acetic acid in water. After 30 min standing in ice, all tubes were centrifuged at 1700 g for 15 min at 4°. The supernatants were poured away, the inner walls of each tube carefully wiped dry and each precipitate redissolved in 0.4 ml 0.1 M triethanolamine HCl buffer, pH 8.0, containing 0.05% (w/v) sodium azide. Aliquots (20 μl) were then applied to fibrin plates in quadruplicate. Fibrin plates were prepared from 0.4% (w/v) human fibrinogen (Kabi, Grade L, Flow Laboratories, Scotland) dissolved in 0.029 M barbitone in 125 mM NaCl, pH 7.4, pipetted (9 ml) into 10×10 cm square plastic dishes (Sterilin) and clotted by rapid mixing with 0.3 ml bovine thrombin (50 NIH units/ml, Parke-Davis, UK.) Plates were incubated at 37° for 18–24h usually, but longer if required, and stained with aqueous bromophenol blue. For each lysis zone, two diameters perpendicular to each other were measured using Vernier calipers. All diameters for each sample were averaged, and this mean converted to fibrinolytic activity by reference to a calibration curve. The latter was obtained by adding known amounts of the compound under test to a stock of plasma pooled from at least ten rats. These standards were processed using the same methods and at the same time as the experimental samples. To construct the calibration curve, diameters (mm) were plotted against $\log_{10}$ concentration of compound. The plasma concentration of compound in each experimental sample was expressed as a percentage of that expected on the basis of the dose given and the assumption of 35 ml plasma/kg body weight for each rat.

(c) Assay of [$^{125}$I]-labelled conjugates in the bloodstream of rats

Aliquots (100 μl) of citrated blood were mixed with 20 μl 1% NaI and 400 μl 20% TCA to precipitate protein-bound 125I. After 30 min on ice, the blood was centrifuged and both supernatant and precipitate counted for $^{125}$I-content. The percentage total counts in the precipitate was calculated to give TCA-precipitable counts. For each conjugate, the radiometric clearance pattern was obtained by plotting TCA-precipitable counts (as % of theoretical) in the blood against time.

(d) Assay of fibrinolytic activity in the bloodstream of guinea pigs

Male Dunkin Hartley guinea pigs (350–450 g) were anaesthetized with urethane (25% w/v solution; 6 ml/kg i.p.). One carotid artery was cannulated for collection of blood samples. One femoral vein was cannulated for injection of heparin (50 U/kg i.v.) and compound under test. Approximately 5 min after heparinization, a predose blood sample (2 ml) was taken and mixed with 0.1 volumes 129 mM trisodium citrate. The compound under test was then injected (1 ml/kg) over 10s. Further blood samples were taken exactly 2, 4, 8, 16, 30, 60 and 90 min later. Heparin treatment (50 U/kg i.v.) was repeated after the 30 min sample to maintain cannula patency. All citrated blood samples were kept on ice until the end of each experiment, then centrifuged at 1700 g for 15 min at 4° to obtain plasma. Each plasma sample was diluted 200-fold in phosphate buffered saline, pH 7.4, containing 0.01% (v/v) Tween 80. Aliquots (30 μl) were then applied to fibrin plates in quadruplicate. Fibrin plates were prepared, run and measured as described in (b) above. The calibration curve was obtained by adding known amounts of the compound under test to the pre-dose plasma of each animal. These standards were processed using the same methods and at the same time as the experimental samples. To construct the calibration curve, diameters (mm) were plotted against $\log_{10}$ concentration of compound. The plasma concentration of compound in each experimental sample was expressed as a percentage of that expected on the basis of the dose given and the assumption of 50 ml plasma/kg body weight for each guinea pig.

An alternative sample preparation method used was as follows: The euglobulin fraction was precipitated by adding 0.1 ml of each plasma to 1.82 ml ice-cold 0.011% (v/v) acetic acid in water. After 30 min standing in ice, all tubes were centrifuged at 1700 g for 15 min at 4° C. The supernatants were poured away, the inner walls of each tube carefully wiped dry and each precipitate redissolved in 0.4 ml phosphate-buffered saline, pH 7.4, containing 0.01% (v/v) Tween 80. Aliquots (30 μl) were then applied to fibrin plates as described above.

(e) SDS polyacrylamide gel electrophoresis

Sodium dodecyl sulphate polyacrylamide gel electrophoresis was performed essentially as described by Laemmli (Nature, 227, 680, 1970) except for the following. A vertical slab gel apparatus (Biorad) was used with typically 4% stacking gels and 8% separating gels. Samples were not reduced by the addition of 2-mercaptoethanol and were kept on ice until application to the gel. Molecular weights were determined by comparison of Rf values obtained on zymography with high and low molecular weight standards (Pharmacia) run on the same gel and protein stained with Coomasie brilliant blue.

Fibrin zymography was essentially as described by Granelli-Piperno and Reich (J. Exp. Med., 148 (1), 223, 1978). Examples 1–3 were analysed using the LKB Multiphor electrophoresis apparatus with the imidazole buffer system (LKB Application Note 306).

Results

Radiometric and fibrin place activity clearance profiles for the conjugates of the Examples are shown in FIGS. 2 to 8, together with the profiles for the corresponding unmodified enzymes.

Figure 1:
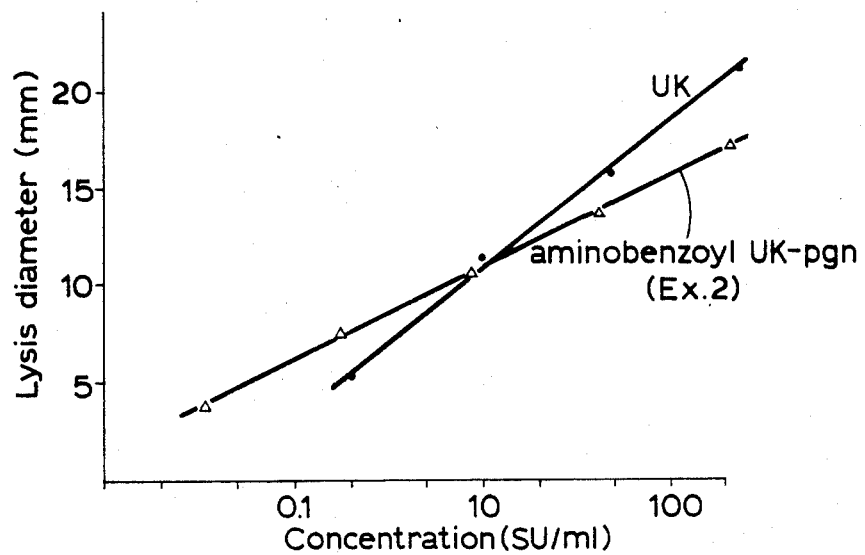
FIG. 1 is a graph showing the fibrin plate activity of urokinase and the aminobenzoyl urokinase-plaminogen conjugate.
Figure 2:
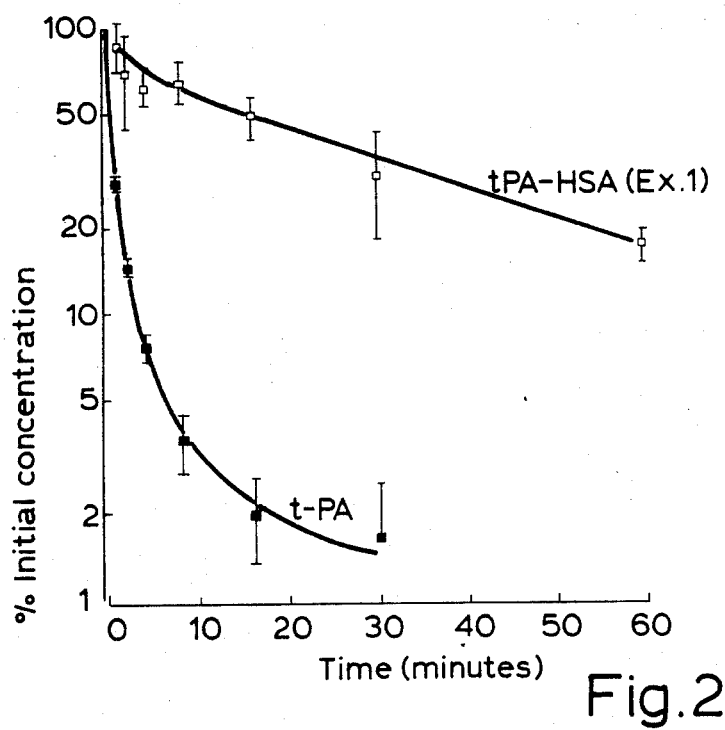
FIG. 2 shows the clearance of fibrin plate activity of tPA and the t-PA-HSA conjugate.
Figure 3:
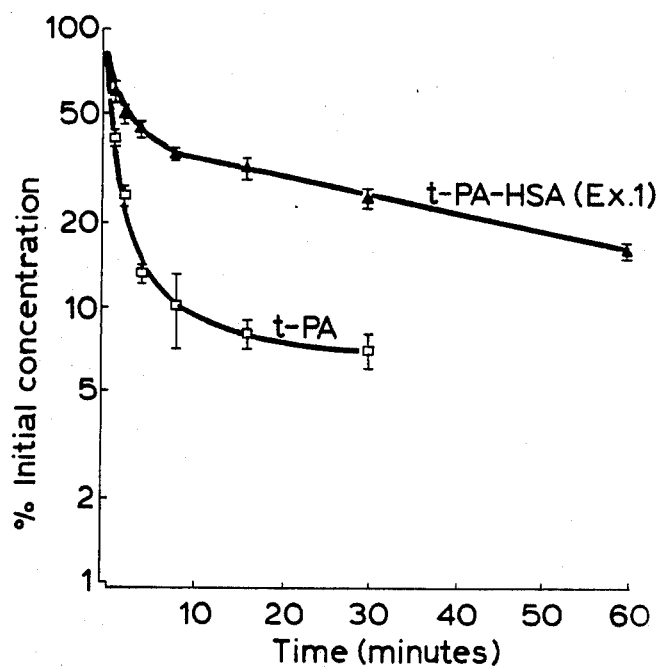
FIG. 3 shows the clearance of TCA precipitable $^{125}$I radioactivity of t-PA and the t-PA-HSA conjugate.
Figure 4:
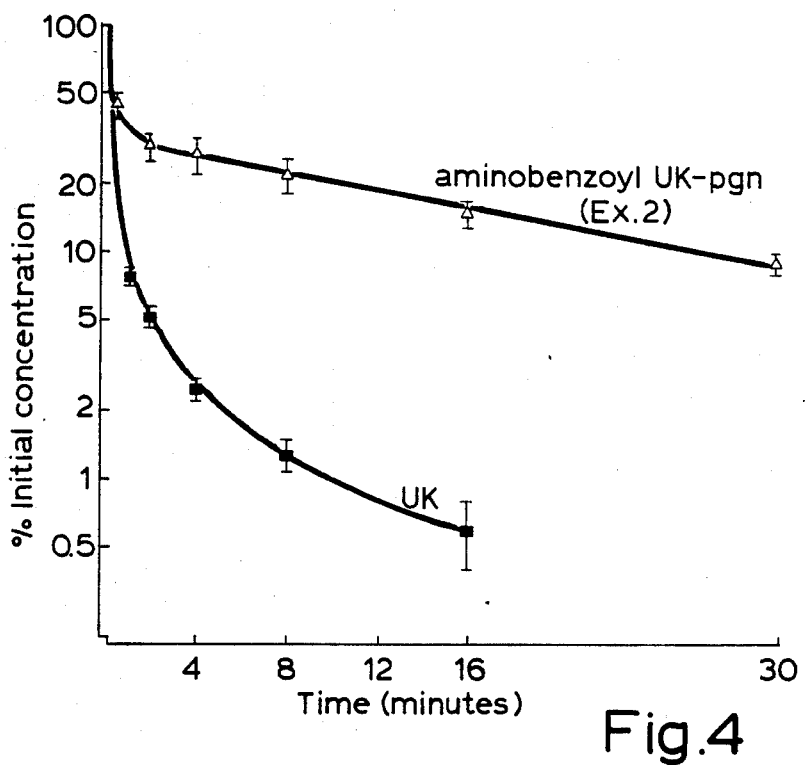
FIG. 4 shows the clearance of fibrin plate activity of urokinase and the 4-aminobenzoyl urokinase-plasminogen conjugate.
Figure 5:
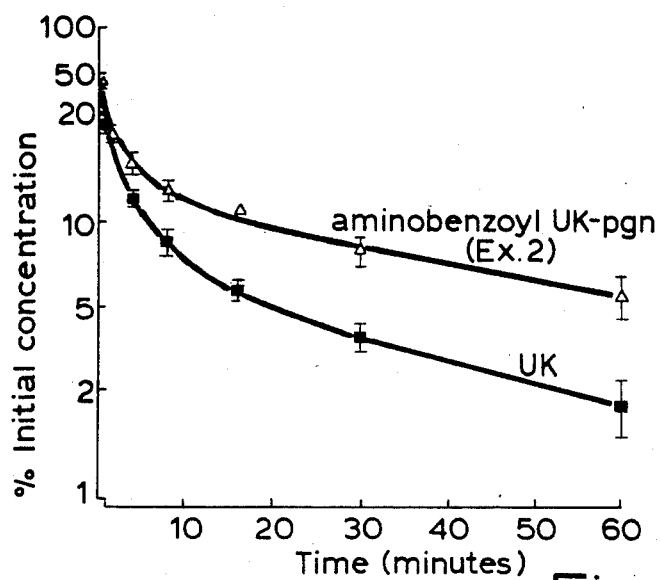
FIG. 5 shows the clearance of TCA precipitable $^{125}$I radioactivity of urokinase and the 4-aminobenzoyl urokinase-plasminogen conjugate.
Figure 6:
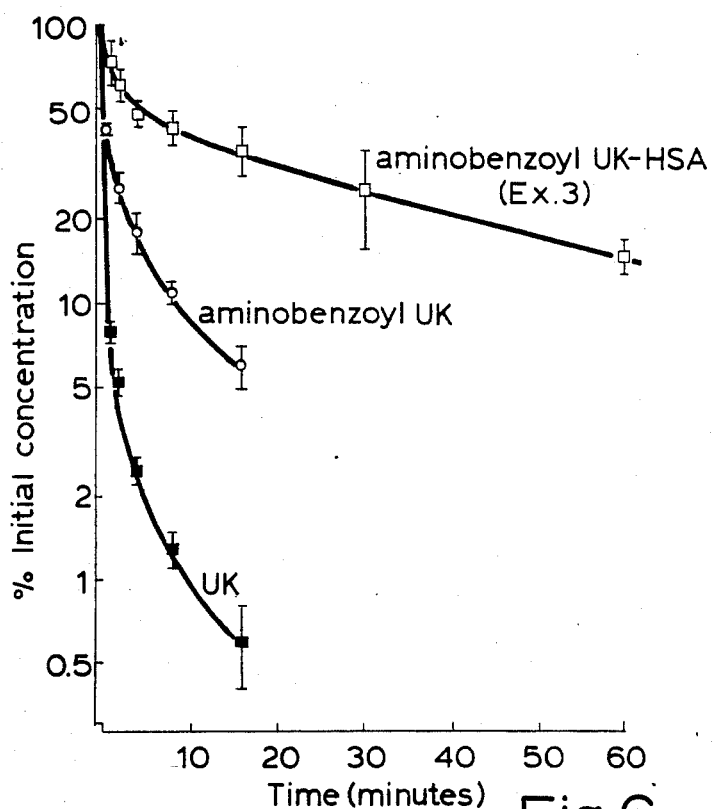
FIG. 6 shows the clearance of fibrin plate activity of urokinase, 4-aminobenzoyl urokinase and the 4-aminobenzoyl urokinase HSA conjugate.
Figure 7:
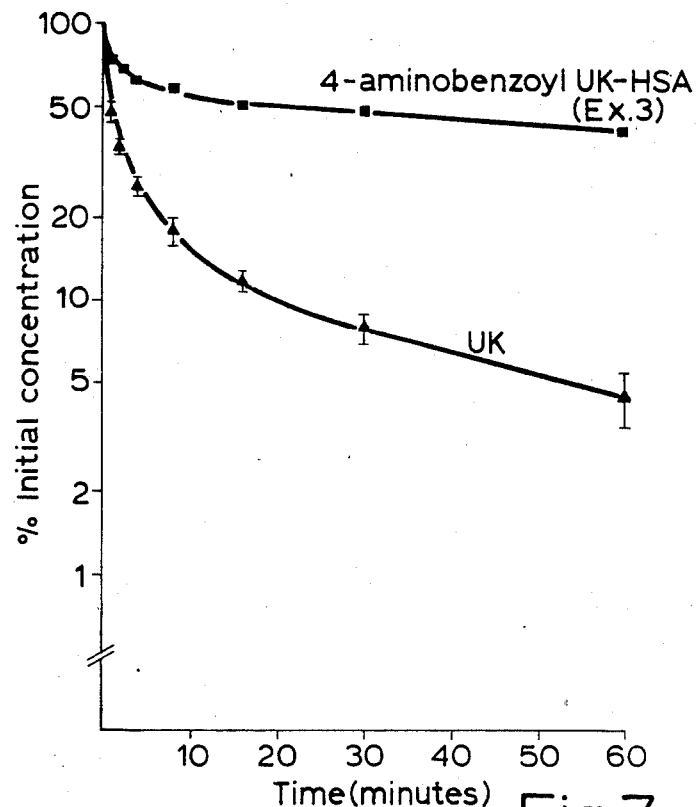
FIG. 7 shows the clearance of TCA precipitable $^{125}$I radioactivity of urokinase and the 4-aminobenzoyl urokinase HSA conjugate.
Figure 8:
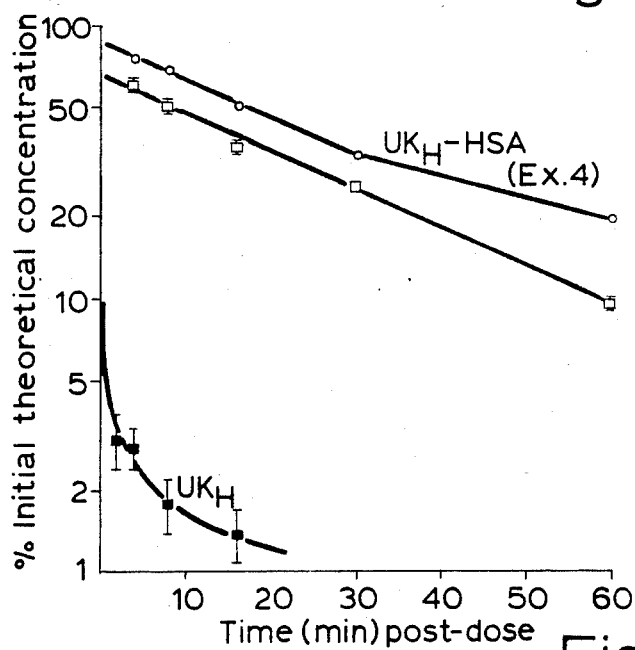
FIG. 8 shows the clearance of high molecular weight urokinase (■) (measured by the euglobulin precipitation method) and of the high molecular weight urokinase-HSA conjugate Example 4 (measure by euglobulin method (0) and dilution method (□))

The profiles clearly show that the conjugates of the Examples are cleared more slowly than the unmodified enzymes. FIG. 6 also shows the clearance of unconjugated 4-aminobenzoyl urokinase. This shows that the slow clearance of the active-site blocked urokinase conjugate is not simply due to the blocking alone.

We claim:

1. A fibrinolytically active protein conjugate comprising at least one optionally blocked fibrinolytic enzyme linked by way of a site other than the catalytic site responsible for the fibrinolytic activity to at least one intact human protein molecule through a bridging group generated by the reaction of a chemically introduced protein attachment group on one said protein with a chemically introduced linking group on the other said protein.

2. A protein conjugate according to claim 1 which comprises one optionally blocked fibrinolytic enzyme linked to one human protein.

3. A protein conjugate according to claim 1 wherein the human protein is a reversibly or irreversibly blocked fibrinolytic enzyme.

4. A protein conjugate according to claim 1 wherein the enzyme is linked to the human protein by a bridging group of formula (I)

—A—R—B—  (I)

in which each of A and B, which may be the same or different, represent

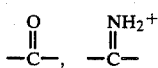

or a bond, and R is a linking group containing one or more —(CH$_2$)— units.

5. A protein conjugate according to claim 1 wherein the fibrinolytic enzyme is selected from tissue-type plasminogen activator or urokinase.

6. A protein conjugate according to claim 1 which is selected from;
Reversibly blocked urokinase linked to human albumin;
Reversibly blocked urokinase linked to plasminogen;
Urokinase linked to human serum albumin;
Urokinase linked to reversibly blocked plasmin;
Reversibly blocked urokinase linked to reversibly blocked plasmin;
Tissue-type plasminogen activator linked to human serum albumin;
Tissue-type plasminogen activator linked to immunoglobulin G;
Tissue-type plasminogen activator linked to reversibly blocked plasmin; and
Tissue-type plasminogen activator linked to fibrinogen.

7. A process for preparing a fibrinolytically active protein conjugate according to claim 1 which process comprises reacting together an optionally blocked fibrinolytic enzyme and a human protein, one of which has been modified to include a protein attachment group and the other of which has been modified to include a linking group having a moiety capable of reacting with the protein attachment group, said enzyme being modified at a site other than the the catalytic site responsible for fibrinolytic activity, and, thereafter, if desired, optionally blocking any fibrinolytic enzyme.

8. A process according to claim 7 wherein the protein attachment group is a reactive thiol group.

9. A pharmaceutical composition comprising a fibrinolytically active protein conjugate according to claim 1 in combination with a pharmaceutically acceptable carrier.

10. A method of treating thrombotic disease which comprises administering to the sufferer an effective non-toxic amount of a fibrinolytically active protein conjugate according to claim 1.

11. A protein conjugate according to claim 1 which is:

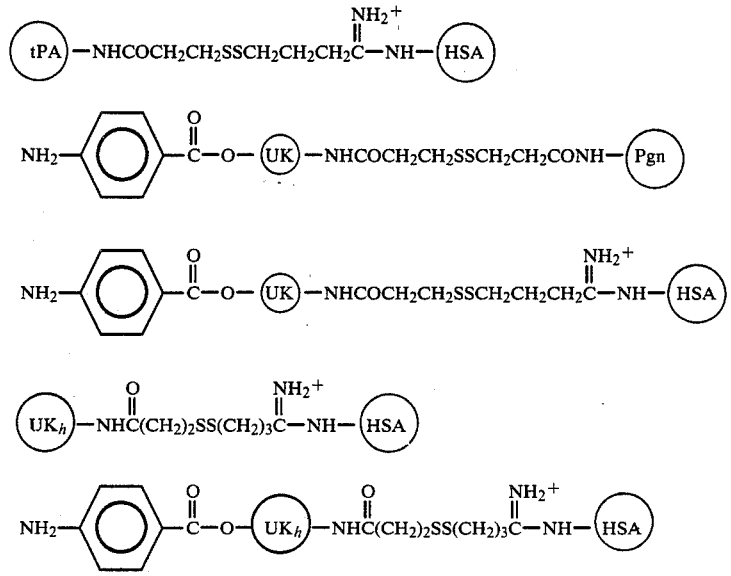

-continued
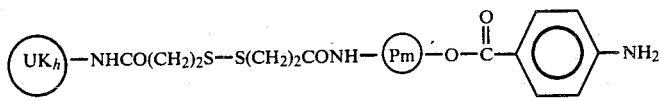
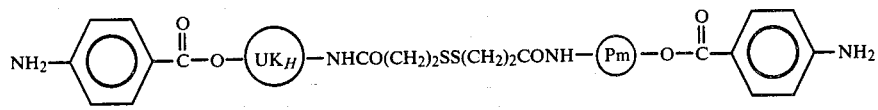
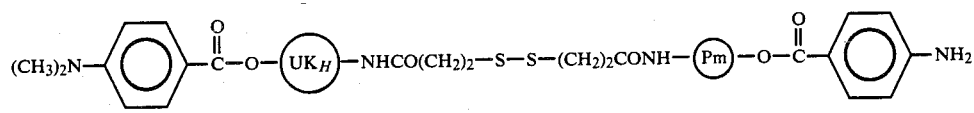
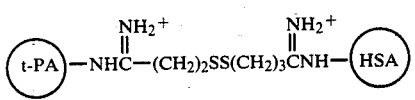
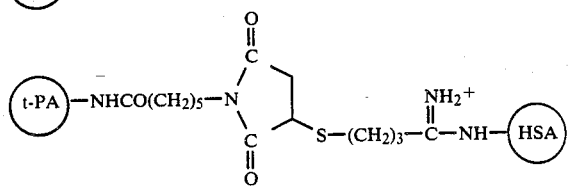
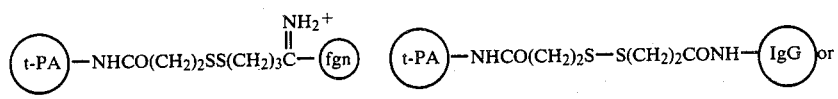
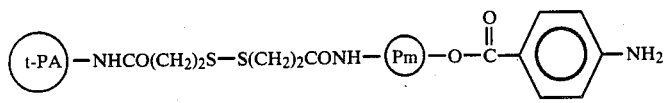
* * * * *